US010370398B2

(12) United States Patent
Dentel et al.

(10) Patent No.: US 10,370,398 B2
(45) Date of Patent: Aug. 6, 2019

(54) LIQUID-LIQUID EXTRACTION OF DMF

(71) Applicant: Tate & Lyle Technology Limited, London (GB)

(72) Inventors: David Dentel, Spanish Fort, AL (US); Thomas Eilers, Arlington Heights, IL (US); Edward Micinski, Martinez, GA (US)

(73) Assignee: TATE & LYLE TECHNOLOGY LIMITED, London (GB)

( * ) Notice: Subject to any disclaimer, the term of this patent is extended or adjusted under 35 U.S.C. 154(b) by 0 days.

(21) Appl. No.: 15/628,141

(22) Filed: Jun. 20, 2017

(65) Prior Publication Data

US 2017/0369518 A1  Dec. 28, 2017

Related U.S. Application Data

(60) Provisional application No. 62/353,838, filed on Jun. 23, 2016.

(51) Int. Cl.
 *C07H 5/02* (2006.01)
 *C07H 1/06* (2006.01)
 *B01D 11/04* (2006.01)
 *C07H 1/00* (2006.01)
 *C07H 13/04* (2006.01)

(52) U.S. Cl.
 CPC .............. *C07H 5/02* (2013.01); *B01D 11/04* (2013.01); *C07H 1/00* (2013.01); *C07H 1/06* (2013.01); *C07H 13/04* (2013.01)

(58) Field of Classification Search
 CPC ............ C07H 5/02; C07H 1/06; B01D 11/04
 USPC ....................................................... 536/127
 See application file for complete search history.

(56) References Cited

U.S. PATENT DOCUMENTS

| | | |
|---|---|---|
| 2,649,481 A | 8/1953 | Caldwell |
| 3,086,050 A | 4/1963 | Notarbartolo et al. |
| 3,294,651 A | 12/1966 | Pasin et al. |
| 3,419,476 A | 12/1968 | Hagedorn |
| 4,380,476 A | 4/1983 | Mufti et al. |
| 4,783,526 A | 11/1988 | O'Brien et al. |
| 4,889,928 A | 12/1989 | Simpson |
| 4,950,746 A | 8/1990 | Navia |
| 4,980,463 A | 12/1990 | Walkup et al. |
| 5,023,329 A | 6/1991 | Neiditch et al. |
| 5,034,551 A | 7/1991 | Vernon et al. |
| 5,089,608 A | 2/1992 | Walkup et al. |
| 5,298,611 A | 3/1994 | Navia et al. |
| 5,440,026 A | 8/1995 | Khan et al. |
| 5,470,969 A | 11/1995 | Sankey et al. |
| 5,498,709 A | 3/1996 | Navia et al. |
| 5,530,106 A | 6/1996 | Navia et al. |
| 5,977,349 A | 11/1999 | Catani et al. |
| 6,646,121 B2 | 11/2003 | El Kabbani et al. |
| 6,809,198 B2 | 10/2004 | El Kabbani et al. |
| 6,890,581 B2 | 5/2005 | Vernon et al. |
| 6,939,962 B2 | 9/2005 | Clark et al. |
| 6,943,248 B2 | 9/2005 | Catani et al. |
| 6,998,480 B2 | 2/2006 | Catani et al. |
| 7,049,435 B2 | 5/2006 | Catani et al. |
| 7,932,380 B2 | 4/2011 | Hao |
| 8,212,022 B2 | 7/2012 | Micinski et al. |
| 8,530,643 B2 | 9/2013 | Boutzale et al. |
| 2003/0171574 A1* | 9/2003 | Catani .................. C07H 1/06 536/119 |
| 2006/0188629 A1 | 8/2006 | Liesen et al. |
| 2006/0205936 A1 | 9/2006 | Jia et al. |
| 2006/0276639 A1 | 12/2006 | Fry |
| 2007/0015916 A1 | 1/2007 | El Kabbani et al. |
| 2007/0100139 A1 | 5/2007 | Fry |
| 2007/0160732 A1 | 7/2007 | Deshpande et al. |
| 2007/0227897 A1 | 10/2007 | Li et al. |
| 2007/0270583 A1 | 11/2007 | Ratnam et al. |
| 2010/0160625 A1 | 6/2010 | Ratnam et al. |
| 2011/0087018 A1 | 4/2011 | Micinski et al. |
| 2012/0077972 A1 | 3/2012 | Boutzale et al. |
| 2012/0095199 A1 | 4/2012 | Hutton et al. |

FOREIGN PATENT DOCUMENTS

| | | |
|---|---|---|
| CA | 749988 A | 1/1967 |
| CN | 1317259 C | 5/2007 |
| CN | 100551903 C | 10/2009 |

(Continued)

OTHER PUBLICATIONS

Maiorov et al., "IR Study of ion-molecular interactions in a DMG—HCl System", Russian Chemical Bulletin, 1993, vol. 42, No. 9, pp. 1511-1516.
Kislina et al., "The Structure of DMF HCl and DMF (HCL)$_2$ Complexes According to ab initio Calculations", Kinetics and Catalysts, 2002, vol. 43, No. 5, pp. 671-674.
Kralj, "Continuous Flow Separation Techniques for Microchemical Synthesis" PhD Thesis, Texas Tech University, 2005, 12 pages.
Saedar, Separation Process Principles, 2nd Edition, 2006, 4 pages.
Lavrova et al., "Extraction of Dimethylformamide in the Presence of Sodium Thiocyanate", Translated from Khimicheskie Volokna, No. 1, pp. 18-19, 1982.

(Continued)

*Primary Examiner* — Yih-Horng Shiao
(74) *Attorney, Agent, or Firm* — RatnerPrestia

(57) ABSTRACT

The present invention relates to a method for the chlorination of a sucrose-6-acylate to produce a 4,1',6'-trichloro-4,1',6'-trideoxy-galactosucrose-6-acylate wherein said method includes steps of:
 (i) combining the sucrose-6-acylate with a chlorinating agent in a reaction vehicle comprising a tertiary amide to afford a mixture;
 (ii) heating said mixture for a heating period in order to provide chlorination of sucrose-6-acylate at the 4, 1' and 6' positions thereof; and
 (iii) quenching the product stream of (ii) to produce a 4,1',6'-trichloro-4,1',6'-trideoxy-galactosucrose-6-acylate;
wherein before said quenching, a portion of said tertiary amide is removed by extraction into a solvent in which said tertiary amide is at least partially soluble.

17 Claims, 1 Drawing Sheet

(56) References Cited

FOREIGN PATENT DOCUMENTS

| | | |
|---|---|---|
| CN | 201840908 U | 5/2011 |
| CN | 202224028 U | 5/2012 |
| CN | 101397260 B | 6/2012 |
| CN | 102503759 B | 10/2013 |
| CN | 103588658 A | 2/2014 |
| CN | 102491870 B | 3/2014 |
| CN | 103772230 A | 5/2014 |
| DE | 2634173 A1 | 3/1977 |
| EP | 0409549 A2 | 1/1991 |
| EP | 0708110 A2 | 4/1996 |
| FR | 2661409 A1 | 10/1991 |
| GB | 715839 | 9/1954 |
| JP | 4854019 A | 7/1973 |
| JP | 4941309 A | 4/1974 |
| JP | 5152116 A | 5/1976 |
| JP | 5170712 A | 6/1976 |
| JP | 62198651 A | 9/1987 |
| JP | 2002001008 A | 1/2002 |
| JP | 3902069 B2 | 4/2007 |
| SU | 1097610 A1 | 6/1984 |
| WO | 2007052305 A2 | 5/2007 |
| WO | 2011045565 A1 | 4/2011 |
| WO | WO 2013/056128 * | 4/2013 |
| WO | 2015092374 A1 | 6/2015 |
| WO | 2016020635 A1 | 2/2016 |

OTHER PUBLICATIONS

Yukhnevich et al., Structure of (DMF)m(HCL)n Complexes (m = 2, n =3-4), Journal of Structural Chemistry, 2005, vol. 46, No. 1, pp. 16-22.

Zhao et al., "Recovery Technology of DMF from Wet Type Polyurethane Synthetic Leather Waste Gas", Chinese Journal of Chemical Engineering, 2008, vol. 16, No. 3, pp. 461-464.

* cited by examiner

LIQUID-LIQUID EXTRACTION OF DMF

CROSS-REFERENCE TO RELATED APPLICATIONS

This application claims priority to U.S. Provisional Application No. 62/353,838 filed Jun. 23, 2016, the entire disclosure of which is incorporated herein by reference for all purposes.

FIELD OF THE INVENTION

The present invention relates to a method of chlorinating a sucrose-6-acylate to produce a 4,1',6'-trichloro-4,1',6'-trideoxy-galactosucrose-6-acylate. In particular, it relates to a method of chlorinating a sucrose-6-acylate to produce a 4,1',6'-trichloro-4,1',6'-trideoxy-galactosucrose-6-acylate and removing some of the tertiary amide reaction vehicle before quench of the reaction.

BACKGROUND OF THE RELATED ART

Methods for producing sucralose intermediates and sucralose from a feed stream comprising a sucrose-6-acylate in a reaction vehicle are known. For example, EP 0409549 discloses a process for the chlorination of a sucrose-6-acylate in a tertiary amide reaction vehicle to produce a sucralose-6-acylate, such as sucralose-6-acetate. A large excess of an acid chloride, such as phosgene, is used as the chlorination agent in this process. Following the chlorination reaction, the excess chlorinating agent is quenched using a suitable base, thereby forming the chloride salt of the base. The resulting product stream thus comprises a sucralose-6-acylate, the tertiary amide reaction vehicle, water, and salts.

A known method for obtaining sucralose from a product stream comprising a sucralose-6-acylate, a tertiary amide reaction vehicle, water, and salts, without isolation of the sucralose-6-acylate intermediate, is disclosed in EP 0708110. The process comprises deacylation of the sucralose-6-acylate before or after removal of the tertiary amide reaction vehicle, and then isolation of the sucralose. Other methods of extraction of sucralose are known, for example, in U.S. Pat. No. 8,212,022.

Methods for preparing sucrose-6-acylate starting materials for chlorination to sucralose-6-acylate are known, for example, in U.S. Pat. Nos. 4,950,746; 4,889,928; 5,023,329; 5,089,608; 5,034,551; 5,470,969; 5,440,026; 6,939,962; and US 2007/0227897.

Other methods of chlorinating sucrose-6-acylate to give sucralose-6-acylate are known, for example, in U.S. Pat. No. 4,380,476; US 2006/0205936; U.S. Pat. No. 7,932,380; and US 2007/0100139.

It is often desirable to recover the reaction solvent after completion of a reaction to minimise waste, or to reuse the solvent. Particularly in sucralose synthesis, it is desirable to recover the tertiary amide from the reaction mixture after chlorination of a sucrose-6-acylate to a sucralose-6-acylate for reuse. U.S. Pat. No. 5,530,106 discloses a method of removing tertiary amide (which is usually N,N-dimethylformamide ("DMF")) from a product mixture after quench by steam stripping.

U.S. Pat. No. 8,530,643 discloses a method of removing DMF from the reaction mixture in the chlorination of a sucrose-6-acylate to a sucralose-6-acylate, before quench of the reaction, by distillation, to afford DMF.

These methods of removing DMF require large amounts of energy to obtain DMF suitable for reuse. Accordingly there is a need for new methods of removing DMF from reaction mixtures.

SUMMARY OF THE INVENTION

According to a first aspect of the present invention, there is provided:

1) A method for the chlorination of a sucrose-6-acylate to produce a 4,1',6'-trichloro-4,1',6'-trideoxy-galactosucrose-6-acylate wherein said method comprises:
   (i) combining the sucrose-6-acylate with a chlorinating agent in a reaction vehicle comprising a tertiary amide to afford a mixture;
   (ii) heating said mixture for a heating period in order to provide chlorination of sucrose-6-acylate at the 4, 1' and 6' positions thereof; and
   (iii) quenching the product stream of (ii) to produce a 4,1',6'-trichloro-4,1',6'-trideoxy-galactosucrose-6-acylate;
   wherein before said quenching, a portion of said tertiary amide is removed by extraction into a solvent in which said tertiary amide is at least partially soluble.

There is Further Provided:
2) A method according to 1), wherein said portion of said tertiary amide is removed after step (i) and before step (ii).
3) A method according to 1), wherein said portion of said tertiary amide is removed after step (ii) and before step (iii).
4) A method according to any of 1) to 3), in which during said extraction, carbohydrates present during or after said reacting of step (i) are substantially not extracted into said solvent.
5) A method according to any of 1) to 4), wherein said solvent is a hydrocarbon.
6) A method according to 5), wherein said solvent is an alkane.
7) A method according to 6), wherein said alkane comprises from 5 to 7 carbon atoms.
8) A method according to 6) or 7), wherein said alkane is straight chain or cyclic.
9) A method according to 5), wherein said solvent is cyclohexane.
10) A method according to any of 1) to 9), wherein said tertiary amide is N, N-dimethylformamide.
11) A method according to any of 1) to 10), wherein said extraction is conducted at a temperature of from 20° to 100° C.
12) A method according to any of 1) to 11), wherein said extraction is performed with a solvent to feed ratio of from 1:1 to 8:1 w/w.
13) A method according to any of 1) to 12), where said portion of tertiary amide removed by extraction is greater than 30 wt % of the total tertiary amide present.
14) A method according to any of 1) to 13), wherein said extraction is performed in a Karr column or a Scheibel column.
15) A method according to any of 1) to 14), wherein after said extraction, said tertiary amide is separated from said solvent by distillation.
16) A method according to any of 1) to 14), wherein after said extraction, said tertiary amide is separated from said solvent by addition of water to form a biphasic system, followed by separation of the two phases.

17) A method according to any of 1) to 16), which further comprises the step of converting at least a portion of said 4,1',6'-trichloro-4,1',6'-trideoxy-galactosucrose-6-acylate to sucralose.
18) A method according to 17), which further comprises the step of isolating and purifying the sucralose.

Further features and advantages of the invention will become apparent from the following description of preferred embodiments of the invention, given by way of example only, which is made with reference to the accompanying drawings.

DETAILED DESCRIPTION OF CERTAIN EMBODIMENTS OF THE INVENTION

Figure 1:
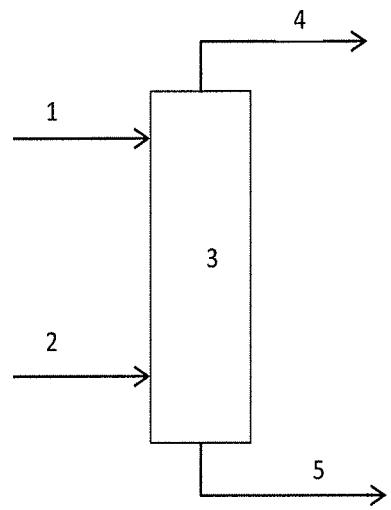
FIG. 1 is a flow diagram which shows a method of extracting a tertiary amide from an unquenched reaction mixture.

A 4,1',6'-trichloro-4,1',6'-trideoxy-galactosucrose-6-acylate can also be referred to as a sucralose-6-acylate, so that 4,1',6'-trichloro-4,1',6'-trideoxy-galactosucrose-6-acetate can also be referred to as sucralose-6-acetate. Both terminologies are used herein.

The sucrose-6-acylate can be any acylate that serves to protect the 6-hydroxy group during the chlorination reaction. It is preferably an aliphatic or carbocyclic aromatic acylate, more preferably a benzoate or acetate, and most preferably an acetate.

As used herein, the term "reaction vehicle" means the diluent or solvent in which the chlorination reaction is performed. The term is meant to indicate that the vehicle may not fully dissolve all the components of the reaction and product mixture. Depending on the chlorinating agent employed, a number of types of reaction vehicles may be used, and any reaction vehicle can be used that is stable under the chlorination conditions and that dissolves the starting materials, reagents, and products at least to some extent. The reaction vehicle according to the present invention comprises a tertiary amide. The tertiary amide reaction vehicle is preferably N,N-dimethylformamide ("DMF"). The ratio by weight of the tertiary amide reaction vehicle, for example DMF, to total carbohydrate during the chlorination reaction may be from about 1.8:1 to about 13:1, or from about 2.5:1 to about 8:1. As used herein, "w/w" means ratio by weight. Unless otherwise specified, ratios given herein are calculated as ratios by weight.

For the avoidance of doubt, in the above "reaction vehicle" is not included any portion that reacts with the chlorinating agent. For example, if the chlorinating agent is Arnold's reagent and the reaction vehicle is DMF, even if the chlorinating agent is added as phosgene which reacts in situ to form Arnold's reagent, those equivalents of DMF are not included in the weight of reaction vehicle for calculating the ratio to carbohydrate.

The reaction vehicle may additionally comprise one or more cosolvents, in addition to the tertiary amide. Suitable cosolvents may be, for example, selected from the group consisting of 1,2-dichloroethane, 1,2-diethoxyethane, toluene, o-xylene, m-xylene, p-xylene, chloroform, dichloromethane, and mixtures thereof. Certain cosolvents such as perfluorooctane, sulfolane, N,N-dimethylacetamide (DMAc) may also be used, as specifically disclosed in WO 2015/092374 and WO 2016/020635. The cosolvent may improve the efficiency and/or the yield of the reaction.

The sucrose-6-acylate and/or the chlorinating agent may be provided in the reaction vehicle.

A number of chlorinating agents may be used in the present invention in order to chlorinate the 4, 1' and 6' positions of the sucrose-6-acylate. Suitable examples include those selected from the group consisting of phosgene, Arnold's reagent (also known as (chloromethylene) dimethyliminium chloride or as (chloromethylene)dimethylammonium chloride), phosphorous oxychloride, phosphorous pentachloride, thionyl chloride, oxalyl chloride, methanesulfonyl chloride, sulfuryl chloride, diphosgene (trichloromethyl chloroformate) and triphosgene (bis(trichloromethyl) carbonate). Other suitable chlorinating agents known to the skilled person may also be used. Preferably, the chlorinating agent is phosgene or Arnold's reagent.

The chlorinating agent is preferably in excess with respect to the sucrose-6-acylate, and preferably in large excess. At least three molar equivalents of chlorinating agent are required per mole of sucrose-6-acylate in order to chlorinate the 4, 1' and 6' positions; thus, an excess amount of chlorinating agent is any amount above three molar equivalents per mole. In a preferred embodiment, the chlorinating agent is provided in an amount of at least seven molar equivalents per mole of the sucrose-6-acylate. Typically, the molar ratio of the chlorinating agent to the sucrose-6-acylate is about 7:1 to about 11:1.

The sucrose-6-acylate and the chlorinating agent are combined in step (i). This is typically conducted at a temperature of from −15 to 55° C., preferably at a temperature of from 0 to 20° C., or from 35 to 45° C.

When the sucrose-6-acylate and the chlorinating agent are combined, the chlorinating agent reacts with the unprotected hydroxyl groups on the sucrose-6-acylate. This is conveniently referred to as "first stage chlorination". For example, when the chlorinating agent is Arnold's reagent, an adduct is formed. The adduct is shown schematically as formula 3 in FIG. 2 of U.S. Pat. No. 4,980,463, which refers to the adduct as "O-alkylformiminium chloride intermediate" (also referred to herein as "Arnold's adduct"). This reaction is rapid at around 15° C. Therefore, the time of holding the resulting mixture is not particularly limited. It may be a few minutes, for example from 5 to 30 minutes, or up to several hours, for example from 5 minutes to 24 hours.

The mixture is then heated to achieve chlorination of sucrose-6-acylate at the 4, 1' and 6' positions thereof in step (ii). This is conveniently referred to as "second stage chlorination". In this process, the adduct is converted into the corresponding chloride. At the 4-position of the sucrose adduct, predominant inversion of stereochemistry occurs. To make sucralose, second stage chlorination is stopped when chloride formation occurs predominantly only at the 4, 1', 6' positions thereof, and the first stage chlorination Arnold's adduct predominantly remains at the other hydroxyl positions (where the second stage chlorination is slower).

A number of reaction conditions can be used to achieve the chlorination. Walkup, U.S. Pat. No. 4,980,463, the disclosure of which is incorporated herein by reference, for example, discloses a two stage process in which chlorination is carried out at two different temperatures, a temperature not higher than about 85° C. and a temperature of at least about 100° C. but not higher than about 130° C. to effect chlorination. Fry, US 2007/0100139, the disclosure of which is incorporated herein by reference, discloses a process in which the reaction mixture is heated between 75° C. to 100° C. to effect chlorination.

In general, the reaction temperature for the chlorination reaction is typically from 85° C. to 130° C. A typical temperature is from 95° C. to 100° C.

The reaction time for the chlorination depends on the temperature employed, with lower temperatures requiring longer reaction times. The skilled person can easily determine the optimum reaction time for a given reaction temperature by monitoring the reaction. If the reaction time is too short, insufficient conversion to the 4,1',6'-trichloro-4,1',6'-trideoxy-galactosucrose-6-acylate occurs. If the reaction time is too long, over-chlorination will occur, resulting in increased levels of tetra-chlorinated by-products. Typical reaction times are from 1 hour to 24 hours.

Once the chlorination reaction has proceeded to the desired stage of completion, there are a number of procedures that may be employed in order to quench the reaction, remove reaction vehicle, and take the material forward to produce sucralose.

At any time before chlorination quench, a portion of the tertiary amide is removed from the reaction mixture by extraction. This can be achieved by liquid-liquid extraction; that is, by extracting a portion of the tertiary amide into a solvent ("the extraction solvent" or "solvent", both terminologies are used herein) in which the tertiary amide is at least partially soluble. The extraction solvent is preferably at least partially immiscible with water.

The unquenched reaction mixture may be referred to as the "feed". Upon extraction of a portion of the tertiary amide from the feed, an extract and a residue mixture are provided. The extract comprises extraction solvent and tertiary amide. The residue mixture comprises carbohydrates, which include the product of the first stage chlorination of sucrose-6-acylate and derivatives thereof in which one, two or three (and at later stages of the second stage chlorination reaction, four) hydroxyl positions have been chlorinated. In one embodiment of the invention, the extract is substantially free of carbohydrates; that is, carbohydrates present in the reaction mixture/feed are substantially not extracted into the extraction solvent.

Suitable extraction solvents may comprise hydrocarbons. In one embodiment, the extraction solvent is an alkane. In further embodiments, the extraction solvent may be an alkane comprising 5 to 7 carbon atoms. In another embodiment, the extraction solvent may be a straight chain alkane, or a cyclic alkane. Suitable extraction solvents include pentane, heptane, hexane, heptane, cyclohexane, methylcyclohexane, diethyl ether, 1-chloropentane, toluene, 1-chlorobutane, and 2-methyl tetrohydrofuran. In a particular embodiment, the extraction solvent is a substituted cyclohexane, or cyclohexane.

In many of the embodiments contemplated herein, the extract portion is removed as the top layer, leaving the residue mixture comprising the carbohydrates as the bottom layer. Therefore, the extraction solvent may have a density of less than the mixture to be extracted.

In a convenient embodiment of the invention, a portion of the tertiary amide can be removed from the reaction mixture after desired completion of the second stage chlorination reaction, immediately before chlorination quench; that is, after step (ii) and before step (iii). A portion of tertiary amide is therefore removed from the unquenched second stage chlorination mass. This is a particularly useful manner in which the tertiary amide can be separated and isolated for recovery and reuse.

In another embodiment, a portion of the tertiary amide can be removed from the reaction mixture after first stage chlorination and before heating the reaction mixture to effect second stage chlorination; that is, after step (i) and before step (ii). A portion of tertiary amide is therefore removed from the first stage chlorination mass.

Optimum conditions for extracting the tertiary amide with an extraction solvent can be determined by the person skilled in the art according to the operating requirements of the process and the equipment used. In one embodiment, the extraction may be conducted at a temperature of from 20° C. to 100° C., or from 50° C. to 70° C., or about 60° C.

The extraction of the tertiary amide may be carried out in a batch or continuous manner. Any suitable manner of liquid-liquid extraction known to the skilled person may be used. In some embodiments, a countercurrent extraction is used. In a batch manner, the extraction of the tertiary amide may be carried out in a separatory funnel, jacketed dropping funnel, or Craig apparatus. In a batch manner, the reaction mixture may be treated with extraction solvent once, or multiple times before quench. In one embodiment, the reaction mixture is extracted at least 5 times, or at least 10 times, before quench.

In a continuous manner, the extraction of the tertiary amide may be carried out in a mixer-settler, extraction column, or centrifugal extractor. Where an extraction column is used, the extraction column may be a static extraction column, agitated extraction column, or pulsed extraction column. In a convenient embodiment of the invention, the extraction of the tertiary amide is carried out in an agitated extraction column. In particular, the extraction may be carried out in a Karr® column, or a Scheibel® column.

An optimum solvent to feed ratio can be determined by the person skilled in the art according to the operating requirements of the process and the equipment used. In one embodiment, the extraction is performed with a solvent to feed ratio of from 1:1 to 8:1 w/w. In a particular embodiment, the solvent to feed ratio is 1:4 w/w.

The method described herein provides an effective way of removing tertiary amide from an unquenched reaction mixture. The portion of tertiary amide removed by extraction according to this method may be greater than 30 wt %, 40 wt % or 50 wt % of the total tertiary amide present in the unquenched reaction mixture.

Notwithstanding the definition of reaction vehicle as discussed above (in which DMF that reacts with chlorinating agent is not accounted as part of the reaction vehicle), when calculating the portion of tertiary amide removed according to the present invention, the total tertiary amide present includes tertiary amide that reacts with the chlorinating agent. Thus "Total DMF", "DMF removed" and equivalent terms refer to and are calculated with respect to the total tertiary amide present, even if tied up during reaction.

Not all of the total tertiary amide present is theoretically extractable. For instance, if the tertiary amide is DMF and the chlorinating agent is phosgene, there will be some DMF tied up in the chlorinating agent. Also, as described above, when second stage chlorination of sucrose-6-acylate is stopped so that chloride formation occurs predominantly only at the 4, 1', 6' positions thereof, the first stage chlorination Arnold's adduct predominantly remains at the other hydroxyl positions (where the second stage chlorination is slower). An amount of DMF therefore will be tied up in this adduct.

Further, without wishing to be bound by any particular theory, a mixture containing DMF and HCl may contain species in which chloride is bound to DMF in the form of a complex. Depending on the concentration of HCl in DMF, it has been postulated that complexes of different $(DMF)_x \cdot (HCl)_y$ stoichiometries may form (Maiorov et al., *Russ. Chem. Bull.*, 1993, 42, 1511-1516). In DMF and HCl mixtures of concentrations as contemplated here, it is postulated that complexes with stoichiometries of $(DMF)_2 \cdot (HCl)$, and to a lesser extent $(DMF) \cdot (HCl)$, are formed. Such complexes are expected not to be soluble in an extraction solvent.

After the extraction of tertiary amide from the reaction mixture, the extract comprising extraction solvent and tertiary amide may be further processed so as to separate the tertiary amide from the extraction solvent. In one embodiment this separation is achieved by distillation. In another embodiment, this separation is achieved by addition of water to form a biphasic system, followed by separation of the two phases. In this embodiment it is especially beneficial to use an extraction solvent with a density of less than the aqueous tertiary amide phase, as this allows the extraction solvent overflow from the separation vessel to be used directly in further extractions.

Following chlorination and removal of a portion of the tertiary amide, the residue mixture may be quenched, for example with a base, to provide a sucralose-6-acylate and the acid salt of the base.

A number of different bases may be used in the quenching. Bases that can be employed for quenching include alkali metal or alkaline earth metal hydroxides, or ammonium hydroxide. As alkali metal hydroxides, sodium and potassium hydroxide are particularly suitable. As an alkaline earth metal hydroxide, calcium hydroxide is particularly suitable. The most usual base for quenching is sodium hydroxide, due to its ready availability and low cost. Other bases known to the skilled person may also be used for quenching. The quench may be performed with an aqueous solution of the base. The aqueous solution may contain from about 5 wt % to about 50 wt %, typically from about 8 wt % to about 40 wt % of the base. Within these ranges, the solution of the base can be either "concentrated" or "dilute". If the solution of the base is concentrated, then precipitation of salts is envisaged, and in this case suitable concentrations are from 13 to 50 wt %, or from 25 to 45 wt %, or about 35 wt %. If the solution of the base is dilute, precipitation of salts is not envisaged, and in that case suitable concentrations are from 5 to 15 wt %, or from 8 to 13 wt %, or from 10 to 11 wt %.

During the quenching, the pH of the mixture may be controlled, since it may be desired that deacylation should be minimised while quenching takes place. This pH control is readily achievable by controlling the addition rate of the aqueous solution of the base while monitoring the pH within the mixture. Any method of pH-controlled addition known to the skilled person may be used.

Suitably, the pH of the mixture is maintained in the range of from about 7.5 to about 10.5 during the quenching, or from about 8.5 to about 10.5, or from about 9.5 to about 10, or from about 9.5 to about 9.75. The pH may also be maintained at a lower level, for example about 4.5, during the addition, and then raised to the desired pH when all of the base has been added. If deacylation is to be carried out as a separate step, though, a pH of more than about 10 should generally be avoided during quenching, since deacylation may then occur. In order to avoid local extremes of pH, the mixture should be adequately mixed throughout the quenching procedure.

The temperature of the mixture during quenching may suitably be maintained in the range of from above 0° C. to about 80° C., for example, in the range of from 10° C. to 60° C., with a range of from about 12° C. to about 35° C. being typical. The quench may be conducted by the "dual stream quench" method, which is described in U.S. Pat. No. 5,530,106 and U.S. Pat. No. 5,498,709.

In the dual stream process, the quenching conditions are attained by slow addition of the aqueous base with simultaneous slow addition of feed material into a reaction vessel. The reaction vessel can contain an initial charge of an aqueous solution of the tertiary amide such as DMF. Slow addition of aqueous base and feed material allows both the pH and the temperature to be controlled during addition. The feed material and aqueous base are simultaneously added slowly until the desired quantity of feed material has been added. Further aqueous base is added until the desired pH is reached. Then the temperature and pH are maintained at the desired levels for the remainder of the reaction. Generally, the pH should not be permitted to rise above about 10.5 during the course of the quenching reaction.

Quenching may alternatively be carried out by a circulated process. In the circulated process, the quenching conditions are attained by circulating feed mixture from a vessel through a circulation loop. Feed mixture and aqueous base are added slowly into this circulation loop. Slow addition of aqueous base and feed material allows both the pH and the temperature to be controlled during addition. Sufficient aqueous base is added until the desired pH is reached. Then the temperature and pH are maintained at the desired levels for the remainder of the reaction. This process may be run in a batch or continuous mode. Generally, the pH should not be permitted to rise above about 10.5 during the course of the quenching reaction.

Following quenching, the mixture may be neutralised by the addition of aqueous acid, for example aqueous hydrochloric acid. The sucralose-6-acylate can then be isolated by conventional means, if desired, or deacylation can be carried out without isolation of the sucralose-6-acylate.

After quenching, or in a combined process with the quenching, at least a portion of the 4,1',6'-trichloro-4,1',6'-trideoxy-galactosucrose-6-acylate can be deacylated to afford sucralose. The deacylation can be performed before or after removal of remaining reaction vehicle.

The deacylation can be carried out, for example, by the method disclosed in U.S. Pat. No. 6,890,581, incorporated herein in its entirety by reference. Other methods for deacylating sucralose-6-acylates, and for isolating and/or purifying sucralose, are disclosed in U.S. Pat. Nos. 5,977,349; 6,943,248 ; 6,998,480; 7,049,435; 6,809,198; 6,646,121, 5,298,611, 5,498,709, US 2006/0188629, US 2006/0276639, US 2007/0015916, US 2007/0160732, and US 2007/0270583, the disclosures of which are all incorporated herein by reference.

The deacylation can be carried out by treatment with a base. Any suitable base may be used, and suitable bases are those already mentioned as the base for quenching. For convenience, the same base may be used for deacylation and quenching. Sodium hydroxide may be used as the base in both cases.

In order to effect deacylation, it is necessary to raise the pH of the mixture, typically to a level above that at which the quenching was carried out. In order to minimise decomposition of the tertiary amide reaction vehicle (if the deacylation is performed before the removal of remaining reaction vehicle), the deacylation may be carried out under carefully controlled conditions. Therefore, the deacylation is preferably performed at a pH of from 10 to 13.5, or from 10 to 12, or from 10.5 to 11.2, at a temperature of from 60 to 0° C., or from 40 to 0° C., or from 35° C. to 25° C., the higher pH being used with the lower temperature and vice versa.

If the deacylation is carried out after removal of remaining reaction vehicle, then the deacylation conditions are less critical, although the above described conditions can still be used. In general, the deacylation may be carried out at a pH of from 8 to 14 and a temperature of from 0 to 60° C., or at a pH of from 10 to 12 and a temperature of from 0 to 40° C.

The deacylation reaction can be conveniently monitored by HPLC. For optimum yields, it is important to monitor the progress of the deacylation reaction, and neutralise the mixture when the reaction is complete. The pH of the mixture should be adjusted to from 6 to 8.5, or approximately 7.5. The mixture can conveniently be neutralised using aqueous hydrochloric acid, or using citric acid or acetic acid. Alternatively, the mixture can be neutralised with gaseous carbon dioxide.

The pH control discussed above in relation to deacylation and subsequent neutralisation is more critical at plant scale; on smaller scales the wider ranges of indicated pH can be employed.

The quenching and deacylation can be carried out in a batch or continuous manner and may be carried out in a single vessel or in multiple vessels. Equally, a combination transitioning between continuous and batch from one or more vessels to one or more vessels can be used. The choice of arrangement will be dictated by practical considerations.

Although quenching and deacylation are carried out sequentially in embodiments described above, it is also possible for quenching and deacylation to be carried out together. In this embodiment, the aqueous solution of a base is added to the chlorination product stream exactly as described above for quenching, but with the exception that the pH of the stream is allowed to rise immediately to a level where deacylation can occur, rather than being controlled to minimise deacylation. Suitable pH conditions for effecting deacylation are discussed above, and are equally applicable here.

The removal of remaining reaction vehicle can be carried out by means known in the art, such as distillation, distillation under reduced pressure, steam distillation, steam stripping, or by use of an agitated thin film drier or spray drier.

If the removal of the reaction vehicle is carried out by steam stripping, then such steam stripping can be carried out as described in EP 0708110. Typically, at least 90% of the reaction vehicle present in the mixture at the end of deacylation (if the removal of the reaction vehicle is carried out after deacylation), or after the quench of the chlorination reaction, (if the removal of the reaction vehicle is carried out before the deacylation) is removed during this step. More typically, at least 99% is removed.

If the mixture is concentrated by distillation, then such distillation will typically remove water and reaction vehicle. Solids may precipitate as a result of the distillation. The solids may include salts, for example sodium chloride. The solids can be filtered and washed with a suitable solvent, for example methanol or ethanol. The solvent such as methanol or ethanol could be removed, for example by flash distillation. This procedure will generally afford the desired sucralose or sucralose-6-acylate in predominantly DMF and aqueous medium. The desired product can be isolated by precipitation or by extraction. Extraction can be performed, for example, by using ethyl acetate or methyl tert-butyl ether.

Alternatively or additionally, before or after quenching and/or deacylation (without removal of remaining reaction vehicle), a partitioning solvent may be used to achieve separation of the components of the mixture. For example, addition of a suitable solvent can be used to partition the components. The partitioning solvent can be, for example, ethyl acetate or tert-butyl methyl ether. The partitioning solvent may be employed in a feed:solvent ratio of from 0.5:1 to 1:3, or from 1:1 to 1:2.

Sucralose-6-acylate can be deacylated to afford sucralose, and sucralose can be purified by known methods, as discussed above.

EXAMPLES

A typical composition of the reaction mixture after step (ii) and before step (iii) of the method described herein (the unquenched second stage chlorination mass) is as follows:

TABLE 1

| Description | % of total, w/w |
|---|---|
| Total Carbohydrates | 8.59 |
| Total Chloride | 13.76 |
| Total DMA (dimethylamine) | 4.86 |
| Total DMF | 63.96 |
| Calculated DMF in (DMF)$_2$•HCl and Arnold's Adduct | 32.08 |
| Calculated Free DMF | 31.88 |
| % of total DMF as free DMF | 49.85 |

Total DMF and total carbohydrates were determined after quenching, but corrected to represent the respective values before quench. The cumulative amount of DMF in (DMF)$_2$.HCl and Arnold's adduct was calculated from chloride analysis after correction was made for chloride in dimethylamine hydrochloride (DMA.HCl). Free DMF present before quenching was calculated by subtracting the amount of DMF in (DMF)$_2$.HCl and Arnold's adduct from the Total DMF.

Example 1

Equal weights of unquenched second stage chlorination mass (Table 1) and extraction solvent were mixed in a flask and agitated with magnetic stirring at ambient temperature. The mixture was transferred to a separatory funnel and the layers allowed to separate. The layers were removed and weighed. The unquenched chlorination mass was processed to crude sucralose solution by quenching with sodium hydroxide. A weighed amount of water was added to the extraction solvent layer ("solv.") and then the extraction solvent removed on a rotary evaporator. The rotary evaporator residue was quenched with 10% NaOH to pH 9.5. Both quenched portions were analysed by HPLC for carbohydrates, ion chromatography for dimethylamine, gas chromatography (GC) for DMF and silver nitrate titration for total chloride. Data from this example is given in Table 2.

TABLE 2

| Extraction solvent | Temperature ° C. | DMF in solv. (% of total DMF) | Carbohydrates in solv. (wt % of solv.) | Chloride in solv. (wt % of solv.) |
|---|---|---|---|---|
| Pentane | 25 | 5.0 | ND | 0.1 |
| Heptane | 25 | 4.6 | ND | 0.1 |
| Cyclohexane | 25 | 5.0 | ND | nm |
| Methyl Cyclohexane | 25 | 4.8 | ND | 0.1 |

TABLE 2-continued

| Extraction solvent | Temperature ° C. | DMF in solv. (% of total DMF) | Carbohydrates in solv. (wt % of solv.) | Chloride in solv. (wt % of solv.) |
|---|---|---|---|---|
| Mixed Hexanes | 25 | 8.1 | ND | nm |
| Diethyl Ether | 25 | 31.8 | 1.2 | nm |
| 1-Chloropentane | 25 | 42.5 | 1.3 | 2.8 |
| Toluene | 25 | 47.1 | 3.1 | nm |
| 1-Chlorobutane | 25 | 57.2 | 2.2 | nm |
| 2-Methyl Tetrahydrofuran | 25 | 67.2 | 3.4 | nm |
| Heptane | 60 | 10.2 | ND | 0.2 |
| Methyl Cyclohexane | 60 | 11.6 | ND | 0.2 |
| 1-Chloropentane | 60 | 50.9 | 1.3 | 3.5 | nm = not measured
ND = not detected

Example 2

Equal weights of unquenched second stage chlorination mass and cyclohexane were mixed in a jacketed dropping funnel maintained at temperatures from 10° C. to 70° C. Agitation was stopped and the layers allowed to separate. The layers were removed and weighed. The lower unquenched chlorination mass was processed to crude sucralose solution by quenching with sodium hydroxide. A weighed amount of water was added to the upper cyclohexane layer and then the cyclohexane removed on a rotary evaporator. Residue from rotary evaporator was quenched with 10% NaOH to pH 9.5. Both quenched portions were analysed by HPLC for carbohydrates, GC for DMF and silver nitrate titration for total chloride. Data from this example is given in Table 3.

TABLE 3

| Temperature (° C.) | DMF in solv. (% of total DMF) | Carbohydrates in solv. (wt % of solv.) | Chloride in solv. (wt % of solv.) |
|---|---|---|---|
| 10 | 2.0 | 0.01 | 0.54 |
| 20 | 4.4 | 0.01 | 0.51 |
| 30 | 5.7 | ND | 0.67 |
| 40 | 8.0 | ND | 0.27 |
| 50 | 10.4 | ND | 0.12 |
| 60 | 14.6 | ND | 0.12 |
| 70 | 16.6 | ND | 0.14 |

Example 3

Equal weights of unquenched second stage chlorination mass and cyclohexane were charged to a jacketed dropping funnel and agitated at a temperature of 60° C. The mixture was allowed to separate while maintaining 60° C. temperature. Both layers were removed and weighed. A sample of the lower unquenched chlorination mass was quenched with 10% NaOH to a pH of 9.5. A weighed amount of water was added to the upper cyclohexane layer and the cyclohexane removed on a rotary evaporator. Residue from rotary evaporator was quenched with 10% NaOH to pH 9.5.

Equal weights of the remaining unquenched chlorination mass and fresh cyclohexane were contacted for extraction again using the method above for a total of 10 extractions. After the final extraction, the lower unquenched chlorination mass was processed to crude sucralose solution by quenching with NaOH. All samples were analysed by HPLC for carbohydrates, GC for DMF and silver nitrate titration for chloride. Data from this example is given in Table 4.

TABLE 4

| Number of extractions | Amount of DMF extracted (% of total DMF) | Amount of Carbohydrates extracted (wt % of solv.) | Amount of Chloride extracted (wt % of solv.) |
|---|---|---|---|
| 1 | 13.4 | ND | 0.06 |
| 7 | 48.0 | ND | 0.05 |
| 8 | 49.9 | ND | 0.06 |
| 9 | 51.4 | ND | 0.07 |
| 10 | 53.1 | ND | 0.06 |

Example 4

Emboldened numbers used in this example refer to the corresponding numbers in FIG. 1. A 120 inch tall jacketed glass Karr® column (3) with 1 inch internal diameter and 2 inches between plates was fed at the top (1) with unquenched second stage chlorination mass and fed at the bottom (2) with cyclohexane. Solvent to feed ratio, total combined feed, and temperature were varied as shown in Table 5. Agitation was varied from 70 to 150 strokes per minute. Samples of the cyclohexane extract (4) were solvent swapped into water and analysed. Bottom residue mixture (5) samples were taken and processed to crude sucralose solution by quenching with NaOH. Percent of DMF extracted was calculated from both the remaining DMF in the bottom residue mixture and the amount of DMF in the cyclohexane extract. Data from this example is given in Table 5.

TABLE 5

| Temperature (° C.) | Total Flow (ml/min) | Solvent to Feed Ratio | % of Total DMF extracted | % Carbohydrate extracted |
|---|---|---|---|---|
| 50 | 260 | 2 | 17.4 | ND |
| 50 | 380 | 2 | 21.0 | ND |
| 60 | 260 | 4 | 39.5 | ND |
| 60 | 380 | 4 | 36.7 | ND |
| 60 | 380 | 6 | 36.8 | ND |
| 65 | 380 | 8 | 38.3 | ND |
| 70 | 260 | 8 | 45.1 | ND |
| 70 | 380 | 4 | 34.4 | ND |
| 70 | 380 | 8 | 31.1 | ND |

Example 5

Emboldened numbers used in this example refer to the corresponding numbers in FIG. 1.

A 100 inch tall glass Scheibel® column (3) with 3 inch internal diameter and 60 stages was fed at the top (1) with unquenched second stage chlorination material and fed at the bottom (2) with cyclohexane. Agitation speed, solvent to feed ratio, total and combined feed were varied as shown in Table 6. Temperature was set at 60° C. Samples of the cyclohexane extract (4) were solvent swapped into water and analysed. Bottom residue mixture (5) samples were taken and processed to crude sucralose solution by quenching with NaOH. Percent of DMF extracted was calculated from both the remaining DMF in the bottom residue mixture and the amount of DMF in the cyclohexane extract. Data from this example is given in Table 6.

TABLE 6

| Total Feed Flow (ml/min) | Agitation (rpm) | Number of stages | Cyclohexane to Feed Ratio | % of Total DMF extracted |
| --- | --- | --- | --- | --- |
| 240 | 200 | 60 | 4 | 47.8 |
| 240 | 400 | 60 | 4 | 48.9 |
| 240 | 500 | 60 | 4 | 51.6 |
| 300 | 200 | 60 | 4 | 43.9 |
| 300 | 300 | 60 | 4 | 47.6 |
| 300 | 400 | 60 | 4 | 42.0 |
| 360 | 200 | 60 | 4 | 49.8 |
| 300 | 300 | 40 | 4 | 39.1 |
| 400 | 300 | 40 | 4 | 39.6 |
| 500 | 300 | 40 | 4 | 44.6 |
| 600 | 300 | 40 | 4 | 43.9 |

Example 6

Figure 2:
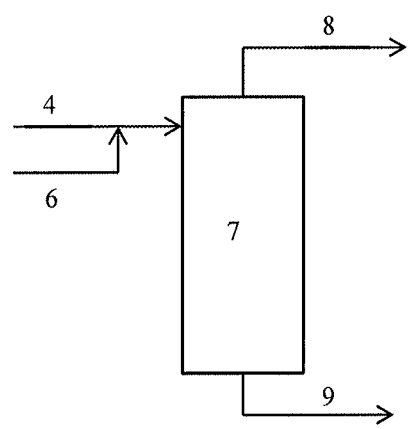
FIG. 2 is a flow diagram which shows a method of separating an extracted tertiary amide from an extraction solvent.

Emboldened numbers used in this example refer to the corresponding numbers in FIG. 2.

The cyclohexane extract (4) from the Karr ® column in Example 4 was cooled to ambient temperature and fed to a decanter (7). The amount of water added (6) was varied as shown in Table 7. The DMF or DMF/water settled out in the decanter and was removed (9). The cyclohexane was allowed to overflow (8) from the top of the decanter and was reused directly in the extractions according to Example 4 without further purification. The DMF (9) was processed to >99% purity by distillation to remove any water using an Oldershaw column under vacuum. Samples were analysed by gas chromatography for DMF. Data from this example is given in Table 7.

TABLE 7

| Water added (wt % relative to cyclohexane feed) | DMF remaining in cyclohexane (% of total mixture, w/w) | DMF removed (% of total amount of DMF in mixture, w/w) |
| --- | --- | --- |
| 0.0 | 4.6 | ND |
| 1.0 | 1.8 | 61.3 |
| 2.5 | 1.0 | 79.4 |
| 3.5 | 0.9 | 80.4 |
| 5.0 | 0.2 | 94.6 |

Runs of extractions according to Example 4 carried out at 65° C. and 4:1 solvent to feed ratio with continuous recycle of cyclohexane (Table 8) showed little difference between fresh cyclohexane and recovered cyclohexane in extracting DMF from unquenched second stage chlorination mass (if at least 1% water (6) was added to the decanter (7)).

TABLE 8

| Cyclohexane source | Water added at decanter | % DMF in extractor bottoms |
| --- | --- | --- |
| New | 0 | 17.3 |
| Recycled | 0 | 20.3 |
| Recycled | 1.0 | 16.0 |
| Recycled | 2.5 | 16.8 |
| Recycled | 3.5 | 16.0 |

Reuse of the DMF from the decanter (7) after only distillation to remove water showed no detrimental effects on chlorination yields when used as the reaction vehicle in the chlorination reaction.

Example 7

Table 9 provides a typical composition of the reaction mixture after step (i) and before step (ii) of the method described herein (the unquenched first stage chlorination mass).

Equal weights of unquenched first stage chlorination mass and cyclohexane were mixed in a flask and agitated with magnetic stirring at ambient or elevated temperatures. The mixture was transferred to a separatory funnel and the layers allowed to separate. The layers were removed and weighed. The lower unquenched chlorination mass, without further treatment, was processed to sucrose/sucrose-ester solution by quenching with sodium hydroxide. A weighed amount of water was added to the upper extraction solvent layer and then the cyclohexane removed on a rotary evaporator. Rotary evaporator residue was quenched with 10% NaOH to pH 9.5. Both quenched portions were analysed by GC for DMF and silver nitrate titration for total chloride. The data from this example is given in Table 10.

TABLE 9

| Description | % of total, w/w |
| --- | --- |
| Total Carbohydrates | 9.6 |
| Total Chlorides | 15.8 |
| Total DMF | 74.5 |
| Calculated DMF in (DMF)$_2$•HCl and Arnold's Adduct | 45.1 |
| Calculated Free DMF | 29.4 |
| % of total DMF as free DMF | 39.5 |

TABLE 10

| | At 25° C. | At 60° C. |
| --- | --- | --- |
| Amount of DMF extracted (% of Total DMF) | 6% | 16.6% |
| Amount of chlorides extracted (% of Total Chlorides) | 0.07% | 0.14% |

The above embodiments are to be understood as illustrative examples of the invention. Further embodiments of the invention are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed:

1. A method for the chlorination of a sucrose-6-acylate to produce a 4,1',6'-trichloro-4,1',6'-trideoxy-galactosucrose-6-acylate wherein said method comprises:
    (i) combining the sucrose-6-acylate with a chlorinating agent in a reaction vehicle comprising a tertiary amide to afford a mixture;
    (ii) heating said mixture for a heating period in order to provide chlorination of sucrose-6-acylate at the 4, 1' and 6' positions thereof; and
    (iii) quenching the product stream of (ii) to produce a 4,1',6'-trichloro-4,1',6'-trideoxy-galactosucrose-6-acylate;
    wherein before said quenching, a step of removing a portion of said tertiary amide is by extraction into an extraction solvent in which said tertiary amide is soluble is performed, wherein said extraction is performed using the extraction solvent to feed ratio of 4:1 to 8:1 w/w, and wherein the mixture is the feed.

2. The method according to claim 1, wherein said portion of said tertiary amide is removed after step (i) and before step (ii).

3. The method according to claim 1, wherein said portion of said tertiary amide is removed after step (ii) and before step (iii).

4. The method according to claim 1, wherein during said extraction, carbohydrates present during or after said reacting of step (i) are not extracted into said extraction solvent.

5. The method according to claim 1, wherein said extraction solvent is a hydrocarbon.

6. The method according to claim 5, wherein said extraction solvent is an alkane.

7. The method according to claim 6, wherein said alkane comprises from 5 to 7 carbon atoms.

8. The method according to claim 6, wherein said alkane is straight chain or cyclic.

9. The method according to claim 5, wherein said extraction solvent is cyclohexane.

10. The method according to claim 1, wherein said tertiary amide is N,N-dimethylformamide.

11. The method according to claim 1, wherein said extraction is conducted at a temperature of from 20° C. to 100° C.

12. The method according to claim 1, wherein said portion of tertiary amide removed by extraction is greater than 30wt% of the total tertiary amide present.

13. The method according to claim 1, wherein said extraction is performed in a Karr column or a Scheibel column.

14. The method according to claim 1, wherein after said extraction, said tertiary amide is separated from said solvent by distillation.

15. The method according to claim 1, wherein after said extraction, said tertiary amide is separated from said solvent by addition of water to form a biphasic system, followed by separation of the two phases.

16. The method according to claim 1, wherein the method further comprises a step of converting at least a portion of said 4,1',6'-trichloro-4,1',6'-trideoxy-galactosucrose-6-acylate to sucralose.

17. The method according to claim 16, wherein the method further comprises a step of isolating and purifying the sucralose.

* * * * *